United States Patent [19]

Grollier et al.

[11] Patent Number: 5,610,201
[45] Date of Patent: Mar. 11, 1997

[54] COSMETIC OR PHARMACEUTICAL COMPOSITION FOR THE TREATMENT OF HAIR AND OF THE SCALP

[75] Inventors: Jean-François Grollier; Isabelle Hansenne-Richoux, both of Paris, France

[73] Assignee: L'Oreal, Paris, France

[21] Appl. No.: 708,379

[22] Filed: May 31, 1991

[30] Foreign Application Priority Data

May 31, 1990 [FR] France .................... 90 06777

[51] Int. Cl.$^6$ .................................... A61K 47/00
[52] U.S. Cl. .................... 514/773; 514/788; 514/975; 424/401
[58] Field of Search .................... 514/773, 788, 514/975; 424/401

[56] References Cited

U.S. PATENT DOCUMENTS

| | | | |
|---|---|---|---|
| 4,772,471 | 9/1988 | Vanlerberghe | 424/450 |
| 5,124,081 | 6/1992 | Vanlerberghe | 424/450 |
| 5,171,577 | 12/1992 | Griat et al. | 424/450 |

FOREIGN PATENT DOCUMENTS

| | | | |
|---|---|---|---|
| 0318369 | 5/1989 | European Pat. Off. | A61K 7/00 |
| 0373988 | 6/1990 | European Pat. Off. | A61K 7/00 |
| 2597367 | 10/1987 | France | B01J 13/02 |
| 2157168 | 10/1985 | United Kingdom | A61K 7/06 |
| 8806881 | 9/1988 | WIPO | A61K 9/50 |

Primary Examiner—Marianne M. Cintins
Assistant Examiner—M. Moezie
Attorney, Agent, or Firm—Cushman Darby & Cushman Intellectual Property Group of Pillsbury Madison & Sutro LLP

[57] ABSTRACT

Cosmetic or pharmaceutical composition for the treatment of hair and of the scalp, obtained by using an aqueous solution containing at least one cationic surface-active agent and/or a quaternized protein, in combination with ionic lipids capable of forming a lipidic lamellar phase.

26 Claims, No Drawings

COSMETIC OR PHARMACEUTICAL COMPOSITION FOR THE TREATMENT OF HAIR AND OF THE SCALP

The present invention relates to a cosmetic or pharmaceutical composition for the treatment of hair and of the scalp.

It is well known that hair is sensitized or made fragile to various degrees by the action of atmospheric agents and by the action of various cosmetic treatments such as permanent waving, dyeing or bleaching. Hair then becomes difficult to untangle and to style. In addition, it becomes rough to the touch.

Compositions which make it possible to facilitate the untangling and the styling of hair and which improve its softness to the touch have therefore been sought after. Cationic surface-active agents are commonly employed for this purpose. The said surface-active agents improve untangling and styling, but present disadvantages: they tend to make hair heavy and to make it look greasy. These disadvantages are proportionately more accentuated the finer the hair which is treated.

It has also been proposed to employ quaternized proteins for the same purpose. The said proteins do not present the disadvantage of making hair heavier or that of making it look greasy; on the other hand, the improvement in untangling and styling hair which they produce is markedly inferior to that produced by cationic surface-active agents.

Attempts have therefore been made to employ compositions containing both a cationic surface-active agent and a quaternized protein. However, in this case, the effect obtained is inferior to the sum of the effects which could be obtained separately with the aid of the cationic surface-active agent and with the aid of the quaternized protein because, in most cases, the deposition of the cationic surface-active agent onto hair retards that of the quaternized protein. It has already been proposed, in GB-A-2,157,168, to remedy this situation by adding a cationic silicone polymer, which appreciably improves the effect obtained on hair.

It has been known for a very long time, furthermore, to employ oils and fatty substances to restore softness and sheen to hair; the application of these compounds is generally followed by shampooing to remove the excess oil or fatty substance from the hair. However, the use of oils and fatty substances softens hair and makes it heavier, and it is consequently impossible to obtain a hairstyle which keeps its shape and has volume.

According to the present invention it has been found that by combining, with an aqueous solution containing at least one particular cationic surface-active agent and/or a quaternized protein, ionic lipids capable of forming a water-insoluble, hydrated lipidic lamellar phase, compositions are obtained which enable hair to be untangled and styled easily without being softened or made heavier or greasy. In addition, the said compositions endow hair with properties which are surprising in respect of fullness and permit hair to be coated from the root to the tip. Treated hair therefore has sheen and softness and, after untangling, is smooth and lightweight from the root to the tip, even in the case of sensitized hair and fine hair. These effects are comparable with those defined by GB-A-2,157,168.

It has also been found, however, that the compositions according to the present invention surprisingly have a hydrating action on the scalp. They have the advantage of providing a pleasant sensation of coolness and of comfort on the scalp. They therefore have a double action: on the hair and on the scalp; this result is quite novel and unexpected.

In addition, the compositions according to the invention have excellent storage stability.

The subject of the present invention is therefore a cosmetic or pharmaceutical composition for the treatment of hair and of the scalp, containing ionic amphiphilic lipids capable of forming a water-insoluble, hydrated lipidic lamellar phase, which are optionally used in combination with a stabilizer, the said lipids being dispersed in a continuous aqueous phase characterized in that the said aqueous phase contains:

1) at least one cationic surface-active agent of formula:

in which formula X is especially chlorine or $CH_3SO_4^-$ and $R_1$ is a $C_1$–$C_4$ alkyl radical, preferably the methyl radical, and in which:
a) when X is chlorine,
either $R_2$ and $R_3$ are $C_1$–$C_4$ alkyl radicals identical with or different from $R_1$ and from each other, and $R_4$ is a $C_{16}$–$C_{22}$ alkyl radical;
or else $R_2 = R_1$ and, in this case:
either $R_3 = R_4 = C_{18}$ alkyl radical;
or $R_3 = (C_{17}$ alkyl )amidopropyl radical and $R_4 = (C_{14}$ alkyl ) acetate radical;
b) when X is $CH_3SO_4^-$:
$R_2$ denotes an (alkyl and/or alkenyl)amidoethyl radical in which the alkyl and/or alkenyl radical is $C_{13}$–$C_{21}$ and is derived from tallow fatty acids;
$R_3$ and $R_4$ together with the nitrogen form a substituted 4,5-dihydroimidazole heterocyclic ring, especially a 2-($C_{13}$–$C_{21}$ alkyl derived from tallow fatty acids)4,5-dihydroimidazole and/or 2) at least one quaternized protein consisting of a chemically modified polypeptide carrying at the end of a chain or grafted onto the latter at least one quaternary ammonium group which contains at least one $C_1$–$C_{18}$ alkyl group, the polypeptide being chosen from animal protein hydrolysates;

provided that, if the composition contains distearyldimethylammoniumchloride as a cationic surface-active agent, the said composition necessarily contains at least one quaternized protein such as defined under 2) above.

When this hydrated lipidic lamellar phase forms vesicles, the latter are called liposomes. The liposomes present in the composition according to the invention advantageously have an average diameter of between 0.01 and 5μ, preferably between 0.05 and 0.35μ.

Liposomes are well known in the state of the art. They are spherules or vesicles consisting of one or more concentric layers of lipids separated by layers of internal aqueous phase. In the case of liposomes, the lipids employed for the manufacture of the spherules or vesicles are, in a known manner, ionic amphiphiles of natural or synthetic origin, comprising one or more long hydrocarbon chains per molecule.

According to the invention, the ionic amphiphilic lipidic compound(s) forming the water-insoluble hydrated lipidic lamellar phase is(are) advantageously chosen from the following compounds:
a) natural or synthetic phospholipids, especially egg or soya lecithin, sphingomyelin, dipalmitoylphosphatidylcholine or hydrogenated lecithin;

b) amphoteric compounds containing two lipophilic chains or a combination of two long-chain organic ions of opposite signs;

c) anionic compounds.

Among anionic compounds, choice is advantageously made of those of formula:

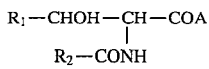

in which formula:

$R_1$ denotes a $C_7$–$C_{21}$ alkyl or alkenyl radical;

$R_2$ denotes a $C_7$–$C_{31}$ saturated or unsaturated hydrocarbon radical;

COA denotes a group chosen from the following groups: COOM, M being H, Na, K, $NH_4$ or a substituted ammonium ion derived from an amine;

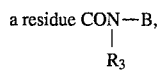

B being a radical derived from mono- or polyhydroxylated primary or secondary amines, and $R_3$ denoting a hydrogen atom or a methyl, ethyl or hydroxyethyl radical;

Q denoting a substituted aminoalkyl or ammonioalkyl radical and $R_3$ having the meaning shown above; and COOZ, Z denoting the residue of a $C_3$–$C_7$ polyol.

In a known manner, these ionic lipidic compounds constituting the hydrated lipidic lamellar phase may be used in combination with at least one stabilizing additive intended to modify the permeability or the surface charge of the lipidic leaflets of the hydrated lipidic lamellar phase. According to the invention, these additives are more particularly chosen from the group made up of sterols, such as cholesterol or beta-sitosterol, monosodium or disodium salts of acyl glutamates, the acyl radical being $C_{14}$–$C_{22}$, such as the monosodium salt of stearoyl glutamate, disodium salts of cocoyl or stearoyl glutamates or of glutamates of mixtures of acyl radicals derived from copra and tallow, phosphoric esters of $C_{12}$–$C_{16}$ fatty alcohols, and lipophilic surfactants such as oxyethylenated phytosterols.

The anionic stabilizers are used in combination with ionic amphiphilic lipid compounds in a quantity preferably not exceeding 12% by weight, relative to the weight of the ionic amphiphilic lipid(s) constituting the hydrated lipidic lamellar phase. In the case of sterols, and especially cholesterol, this same proportion must remain lower than or equal to 100% by weight.

According to the invention, the hydrated lipidic lamellar phase contains water in the presence or absence of a cosmetically or pharmaceutically active agent. By way of active agent there may be mentioned, for example, hair loss-preventing or growth-stimulating agents, retinoids and related substances, antiinflammatories, antifungals, antiseborrhoeics, sunscreens, and the like.

The cationic surface-active agent present, according to the invention, in the continuous aqueous phase of the composition is advantageously chosen from the group made up of:

a) tetraalkylammonium halides such as behenyltrimethylammoniumchloride, distearyldimethylammonium chloride, and trimethylcetylammoniumchloride;

b) stearamidopropyldimethyl(myristylacetate)ammonium chloride of formula:

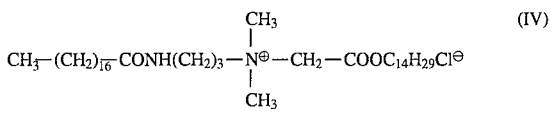

such as the product sold by Van Dyk under the trade name "Ceraphyl 70";

c) a quaternary ammonium salt of formula:

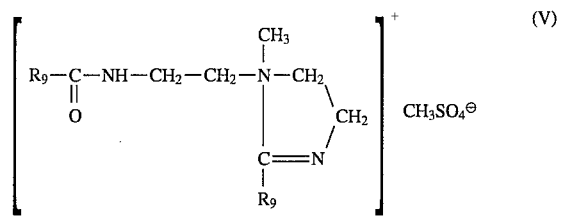

in which $R_9$ denotes a mixture of $C_{13}$–$C_{21}$ alkenyl and/or alkyl radicals derived from tallow fatty acids, such as the product sold by Rewo under the trade name "Rewoquat W 7500".

The quaternized protein present according to the invention in the continuous aqueous phase is advantageously chosen from the group made up of:

a) certain protein hydrolysates carrying, on the polypeptide chain, quaternary ammonium groups containing at least one $C_1$–$C_{18}$ alkyl radical and especially an animal protein hydrolysate sold by Croda under the trade name "Crotein Q", whose polypeptide chain has an average molecular weight of the order of 12,000;

b) animal protein hydrolysates carrying trimethylbenzylammonium groups (called "benzyltrimonium hydrolysed animal protein" in the CTFA Cosmetic Dictionary (3rd edition, 1982) published by the Cosmetic Toiletry and Fragrance Association Inc. and called "CTFA dictionary" hereinafter) and, for example, that sold by Croda under the trade name "Crotein BTA";

c) collagen hydrolysates carrying triethylammonium groups, called "Triethonium hydrolysed collagen ethosulfate" in the CTFA dictionary and sold by Maybrook under the trade name of "Quat-Pro E";

d) collagen hydrolysates carrying trimethylammonium and trimethylstearylammonium groups, called "Steartrimonium hydrolysed collagen" in the CTFA dictionary and sold by Maybrook under the trade name "Quat Pro S";

e) a quaternized protein resulting from the condensation of cocamidopropyl-dimethyl-amine onto a hydrolyzed animal protein, called, in the supplement to the 3rd edition (1982) of the CTFA dictionary: COCAMIDOPROPYLDIMONIUM HYDROXYPROPYLAMINO HYDROLYSED ANIMAL PROTEIN, sold by Inolex under the trade name "Lexein QX 3000".

The compositions according to the invention may preferably contain at least one cationic surfactant and at least one quaternized protein at the same time. In this case:

the cationic surface-active agent is preferably a tetraalkylammonium chloride of formula (I) in which $R_1$, $R_2$ and $R_3$ are $C_1$–$C_4$ alkyl radicals and $R_4$ is a $C_{20}$–$C_{22}$ alkyl radical;

and the quaternized protein is preferably an animal protein hydrolysate carrying quaternary ammonium groups containing a $C_1$–$C_{18}$ alkyl radical.

The continuous aqueous phase of the dispersion may optionally contain, in addition to the cationic surface-active agent and/or the quaternized protein, at least one known additive such as preserving agents, stabilizers, colorants, perfumes, softeners, humectants chosen, preferably, from polyols such as glycerine, and thickeners, such as fatty alcohols, oxyethylenated or otherwise.

In the composition according to the invention the cationic surface-active agent(s) represents(represent) from 0.05 to 10% by weight, preferably from 0.1 to 6% by weight, relative to the total weight of the composition; the quaternized protein(s) represents(represent) from 0.05 to 3% by weight, preferably from 0.05 to 0.5% by weight, relative to the total weight of the composition; the ionic amphiphilic lipid(s) which constitutes(constitute) the lamellar phase represents(represent) from 0.1% to 20% by weight, preferably from 1% to 10% by weight, and more particularly 3 to 10% by weight, relative to the total weight of the composition.

It is obvious that, in the case where a large quantity of cationic surface-active agent(s) is/(are) employed relative to the ionic amphiphilic lipid(s), the choice of the cationic agent(s) is not without consequence and must be made so that it(they) does(do) not destroy the vesicles.

The composition according to the invention is generally prepared by mixing two constituents (A) and (B). The constituent (A) contains the hydrated lipidic lamellar phase in a continuous aqueous phase. The constituent (B) contains the cationic agent and/or the quaternized protein, in aqueous phase. Each of the constituents may additionally contain various additives. It is preferable that each of the constituents (A) and (B) should represent 40 to 60% by weight relative to the total weight of the composition; the two mixed constituents advantageously have substantially the same weight.

The constituent (A) is prepared in a conventional way and more particularly according to the process described in French Patent No. 2,315,991;

in a first stage the ionic amphiphilic lipids, optionally mixed with additives intended to modify the permeability or the charge of the lipidic leaflets of the hydrated lipidic lamellar phase which it is intended to form are brought into contact with water;

in a second stage an aqueous dispersion phase is added to the hydrated lipidic lamellar phase thus obtained;

in a third stage the mixture is subjected to energetic stirring to obtain vesicles.

Once the constituent (B) has been prepared, it is added to the constituent (A) with stirring until complete homogenization takes place.

The compositions according to the invention are preferably applied in the form of products to be rinsed off, before and more particularly after shampooing, before and more particularly after dyeing or bleaching, and before and more particularly after permanent waving or straightening. They may also be applied in the form of products which are not rinsed off, for example before setting or blow-drying.

To make use of the compositions according to the invention with a view to treatment of hair and/or of the scalp, an effective quantity of the composition according to the invention is applied onto the substrate to be treated, is left in contact for 1 to 15 min before being rinsed off when a product to be rinsed off is involved. The appropriate quantities of composition are generally of the order of 20 to 40 g per head in the case of products to be rinsed off and of the order of 5 to 10 g in the case of products which are not rinsed off.

The examples given below, purely by way of illustration and without any limitation being implied, will allow the invention to be better understood.

EXAMPLE 1

In a first stage a constituent (A) comprising vesicles is prepared. 4 g of soya lecithin containing 75% of phosphatidylcholine sold by SEPPIC under the name "Lipold S 75" are mixed, by stirring gently on a water bath of 60° C., until perfect homogenization takes place (5 min).

8 g of water heated to 80° C. and containing preserving agents are introduced into the mixture and are mixed for approximately 5 min; the mixture is allowed to swell for 1 hour. 12 g of water at 20° C. are added to the phase thus obtained; the mixture is stirred for a few minutes and the mixture is then refined by being put through a high-pressure homogenizer at 500 bars (Rannie). It is made up with 0.65 g of water at 20° C. with stirring.

In a second stage a constituent (B) is prepared by mixing the following formulations B1 and B2:
Formulation B1:

| Formulation B1: | |
| --- | --- |
| Cetyl alcohol/stearyl alcohol (30/70) | 3.36 g |
| Cetyl alcohol/stearyl alcohol oxyethylenated with 33 moles of ethylene oxide | 0.84 g |
| 2-Octyldodecanol | 0.6 g |
| Cetyl alcohol/stearyl alcohol (50/50) | 1.8 g |

Formulation B2:

| Formulation B2: | |
| --- | --- |
| Glycerine | 0.6 g |
| Distearyldimethylammonium chloride | 4.7 g |
| Collagen hydrolysate containing triethylammonium groups, sold by Maybrook under the name "Quat Pro E" containing 28% of active substances (= AS) | 0.15 g AS |
| Preserving agents | q.s. |
| Water q.s. | 68.4 g |

Mixing of the formulations B1 and B2 is carried out with stirring and the mixture is kept stirred until completely cooled.

In a third stage the mixture of the constituent A and of the constituent B is produced and is kept stirred until completely homogenized.

This composition is applied at a rate of approximately 25 g to the scalp and washed and roughly dried hair. After being left on for 10 minutes it is rinsed off with water. A sensation of coolness is experienced on application to the scalp. After drying it can be seen that the hair is coated and that the hairstyle is lightweight and has body. The hair untangles easily and is shiny, soft and smooth right down to the tips.

EXAMPLE 2

In a first stage a constituent (A) comprising the vesicles is prepared. A mixture of 2 g of soya phospholipids sold by Nattermann under the name "Phospholipon 80" and of preserving agents is mixed by stirring gently at a temperature of 60° C. until perfectly homogenized (5 min).

4 g of water heated to 80° C. and containing a preserving agent are introduced into the mixture and after mixing for approximately 5 min the mixture is left to swell for 1 hour. 6 g of water at 20° C. are added to the phase thus obtained; the mixture is stirred for a few minutes and the mixture is then refined by being put through a high-pressure homogenizer at 500 bars (Rannie); it is made up with 0.325 g of water at 20° C. with stirring.

In a second stage a constituent (B) is prepared by mixing the following formulations B1 and B2:

Formulation B1:

| Formulation B1: | |
|---|---|
| Cetyl alcohol/stearyl alcohol (30/70) | 3.92 g |
| Cetyl alcohol/stearyl alcohol oxyethylenated with 33 moles of ethylene oxide | 0.98 g |
| 2-Octyldodecanol | 0.7 g |
| Cetyl alcohol/stearyl alcohol (50/50) | 2.1 g |

Formulation B2:

| Formulation B2: | |
|---|---|
| Glycerine | 0.7 g |
| Quaternary ammonium salt containing 75% of AS sold by Rewo under the trade name "Rewoquat 7500 PG" | 5 g AS |
| Quaternized protein resulting from the condensation of cocamidopropyl-dimethyl-amine onto a hydrolysed animal protein, sold at a concentration of 30% of AS by Inolex under the trade name "Lexein QX 3000" | 0.2 g AS |
| Preserving agents | q.s. |
| Water q.s. | 79.8 g |

Formulations B1 and B2 are mixed with stirring and the mixture is kept stirred until completely cooled.

In a third stage, constituent A and constituent B are mixed and the mixture is kept stirred until completely homogenized.

This composition is applied at a rate of approximately 25 g to the scalp and washed and roughly dried hair. After being left on for 10 minutes it is rinsed off with water. A sensation of coolness is experienced on application to the scalp. After drying it can be seen that the hair is coated and that the hairstyle is lightweight and has body. The hair untangles easily and is shiny, soft and smooth right down to the tips.

EXAMPLE 3

A constituent (A) comprising the vesicles is prepared in a first stage. 4 g of phytosterol polyoxyethylenated with 5 moles of ethylene oxide, sold by Nikko under the name "Generol 122 E 5" are melted by stirring gently at a temperature of 85° C. A mixture of 6 g of hydrogenated lecithin containing 30–35% of hydrogenated phosphatidylcholine, sold by Nikko under the name "Lecinol S 10" is then added to the molten mixture until perfect homogenization takes place (5 min).

20 g of water heated to 80° C. and containing a preserving agent are added to the molten mixture and after mixing for approximately 5 min the mixture is allowed to swell for 1 hour. 30 g of water at 20° C. are added to the phase thus obtained. The mixture is stirred for a few minutes and is refined by being put through a high-pressure homogenizer at 500 bars (Rannie or Gaulin) and is made up with 9.3 g of water at 20° C. with stirring.

In a second stage a constituent (B) is prepared by mixing the following formulations B1 and B2:

Formulation B1:

| Formulation B1: | |
|---|---|
| Cetyl alcohol/stearyl alcohol (30/70) | 2.24 g |
| Cetyl alcohol/stearyl alcohol oxyethylenated with 33 moles of ethylene oxide | 0.56 g |

-continued

| Formulation B1: | |
|---|---|
| 2-Octyldodecanol | 0.4 g |
| Cetyl alcohol/stearyl alcohol (50/50) | 1.2 g |

Formulation B2:

| Formulation B2: | |
|---|---|
| Glycerine | 0.4 g |
| Behenyltrimethylammonium chloride containing 80% of AS, sold by Hoechst under the name "Genamin KDMF" | 2.75 g AS |
| Protein hydrolysate containing a poly-peptide chain with a molecular weight of approximately 12,000 and quaternary ammonium groups carrying at least one $C_1$–$C_{18}$ alkyl group, sold by Croda under the trade name "Crotein Q" | 0.125 g |
| Preserving agents | q.s. |
| Water q.s. | 25.6 g |

Formulations B1 and B2 are mixed with stirring and the mixture is kept stirred until completely cooled.

In a third stage, constituent A and constituent B are mixed and the mixture is kept stirred until completely homogenized.

This composition is applied in a quantity of approximately 25 g to the scalp and to washed and roughly dried hair. After being left on for 10 minutes it is rinsed off with water. A sensation of coolness is experienced on application to the scalp. After drying it can be seen that the hair is coated and that the hairstyle is lightweight and has body. The hair untangles easily and is shiny, soft and smooth right down to the tips.

EXAMPLE 4

A constituent (A) containing the vesicles is prepared in a first stage. 6 g of soya lecithin containing 75% of phosphatidylcholine, sold by Seppic under the name "Lipoid S 75" are mixed by stirring gently on a water bath at 60° C. until perfectly homogenized (5 min).

12 g of water heated to 80° C., containing preserving agents, are added to the mixture and mixing is continued for approximately 5 min; the mixture is allowed to swell for 1 hour. 18 g of water at 20° C. are added to the phase thus obtained; the mixture is stirred for a few minutes and the mixture is then refined by being put through a high-pressure homogenizer at 500 bars (Rannie). It is made up to 50 g with water at 20° C., with stirring.

In a second stage a constituent (B) is prepared by mixing the following formulations B1 and B2:

Formulation B1:

| Formulation B1: | |
|---|---|
| Cetyl alcohol/stearyl alcohol (30/70) | 3.36 g |
| Cetyl alcohol/stearyl alcohol oxyethylenated with 33 moles of ethylene oxide | 0.84 g |
| 2-Octyldodecanol | 0.6 g |
| Cetyl alcohol/stearyl alcohol (50/50) | 1.8 g |

Formulation B2:

| Formulation B2: | |
| --- | --- |
| Glycerine | 0.6 g |
| Collagen hydrolysate containing trimethylammonium and trimethylstearylammonium groups, sold by Maybrook under the name "Quat Pro S" at a concentration of 90% of AS | 0.5 g AS |
| Preserving agents | q.s. |
| Water q.s. | 50 g |

Formulations B1 and B2 are mixed with stirring and the mixture is kept stirred until completely cooled.

In a third stage, constituent A and constituent B are mixed and the mixture is kept stirred until completely homogenized.

This composition is applied to the scalp and to washed and roughly dried hair; it has the same advantage as that obtained in Example 1.

EXAMPLE 5

An antidandruff cream is prepared:

A constituent (A) containing the vesicles is prepared in a first stage. 4 g of soya phospholipids sold by Nattermann under the name "Phospholipon 80" and 0.2 g of the ethanolamine salt of 1-hydroxy-4-methyl-6-(2,4,4-trimethyl-)pentyl-1H-2-pyridone sold by Hoechst under the name "Octopirox" and preserving agents are mixed by stirring gently at a temperature of 60° C. until perfectly homogenized (5 min).

8 g of water heated to 80° C. and containing a preserving agent are introduced into the mixture and after mixing for approximately 5 min the mixture is allowed to swell for 1 hour. 12 g of water at 20° C. are added to the phase thus obtained, the mixture is stirred for a few minutes and is then refined by being put through a high-pressure homogenizer at 500 bars (Rannie) and is made up to 25 g with water at 20° C., with stirring.

In a second stage a constituent (B) is prepared by mixing the following formulations B1 and B2:
Formulation B1:

| Cetyl alcohol/stearyl alcohol (30/70) | 3.36 g |
| --- | --- |
| Cetyl alcohol/stearyl alcohol oxyethylenated with 33 moles of ethylene oxide | 0.84 g |
| 2-Octyldodecanol | 0.6 g |
| Cetyl alcohol/stearyl alcohol (50/50) | 1.8 g |

Formulation B2:

| Formulation B2: | |
| --- | --- |
| Glycerine | 0.6 g |
| Collagen hydrolysate containing triethylammonium groups, sold by Maybrook under the name "Quat Pro E" at a concentration of 28% of AS | 0.25 g AS |
| Quaternary ammonium salt sold at a concentration of 75% of AS by Rewo under the trade name "REWOQUAT 7500 PG" | 2 g AS |
| Preserving agents | q.s. |
| Water q.s. | 75 g |

Formulations B1 and B2 are mixed with stirring and the mixture is kept stirred until completely cooled.

In a third stage, constituent A and constituent B are mixed and the mixture is stirred until completely homogenized.

After twice-weekly applications for 3 months a reduction in the number of scales is noted.

The cosmetic effect on hair is the same as that described in Example 1.

EXAMPLE 6

A constituent (A) containing the vesicles is prepared in a first stage. 3.04 g of phytosterol polyoxyethylenated with 5 moles of ethylene oxide, sold by Nikko under the name "Generol 122 E 5" are melted by stirring gently at a temperature of 85° C. 4.56 g of hydrogenated lecithin containing 30–35% of hydrogenated phosphatidylcholine, sold by Nikko under the name "Lecinol S 10" are then added to the molten mixture until perfectly homogenized (5 min).

15.2 g of water heated to 80° C. containing a preserving agent are introduced into the molten mixture and after mixing for approximately 5 min the mixture is allowed to swell for 1 hour. 22.8 g of water at 20° C. are added to the phase thus obtained; the mixture is stirred for a few minutes and is refined by being put through a high-pressure homogenizer at 500 bars (Rannie or Gaulin) and is then made up to 50 g with water at 20° C., with stirring.

In a second stage a constituent (B) is prepared by mixing the following formulations B1 and B2:
Formulation B1:

| Formulation B1: | |
| --- | --- |
| Cetyl alcohol/stearyl alcohol (30/70) | 3.36 g |
| Cetyl alcohol/stearyl alcohol oxyethylenated with 33 moles of ethylene oxide | 0.84 g |
| 2-Octyldodecanol | 0.6 g |
| Cetyl alcohol/stearyl alcohol (50/50) | 1.8 g |

Formulation B2:

| Formulation B2: | |
| --- | --- |
| Glycerine | 0.6 g |
| Trimethylcetylammonium chloride containing 25% of AS | 1 g AS |
| Preserving agents | q.s. |
| Water q.s. | 50 g |

Formulations B1 and B2 are mixed with stirring and the mixture is kept stirred until completely cooled.

In a third stage, constituent A and constituent B are mixed and the mixture is stirred until completely homogenized.

This composition is applied to the scalp and to washed and roughly dried hair; it has the same advantages as the composition of Example 1.

We claim:

1. A cosmetic or pharmaceutical composition for the treatment of the hair and scalp comprising an ionic amphiphilic lipid capable of forming a water-insoluble hydrated lipidic lamellar phase, optionally in combination with a stabilizer, said lipid being in a dispersed form in a continuous aqueous phase containing:

(1) at least one cationic surface active agent having the formula

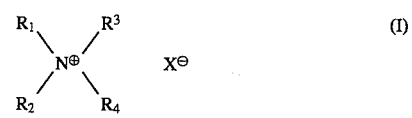

wherein

X is chlorine or $CH_3SO_4^-$ and $R_1$ is a $C_1$–$C_4$ alkyl radical and wherein (a) when X is chlorine,
(i) either $R_2$ and $R_3$ are $C_1$–$C_4$ alkyl radicals identical with or different from $R_1$ and from each other and $R_4$ is a $C_{16}$–$C_{22}$ alkyl radical;
or
(ii) $R_2=R_1$ and
(i') either $R_3=R_4=C_{18}$ alkyl radical, or
(ii') $R_3=(C_{17}$ alkyl) amidopropyl radical and $R_4=(C_{14}$ alkyl) acetate radical and
(b) when X is $CH_3SO_4^-$
$R_2$ represent an (alkyl) amidoethyl radical, an (alkenyl) amidoethyl radical or an (alkylalkenyl) amidoethyl radical wherein each of the alkyl and alkenyl moieties is a $C_{13}$–$C_{21}$ radical and is derived from tallow fatty acids, and
$R_3$ and $R_4$ together with the nitrogen atom to which they are attached form a 4,5-dihydroimidazole ring substituted in position 2;
or
(2) at least one quaternized protein consisting of a chemically modified polypeptide carrying at the end of a chain or grafted onto the latter at least one quaternary ammonium group containing at least one $C_1$–$C_{18}$ alkyl chain, said polypeptide being an animal protein hydrolyzate,
or both (1) and (2) defined above,
with the proviso that when said composition contains distearyldimethylammonium chloride as a cationic surface active agent, said composition necessarily contains at least one quaternized protein defined in (2) above.

2. The composition of claim 1 wherein said hydrated lipidic lamellar phase is present in the form of vesicles.

3. The composition of claim 2 wherein said vesicles have an average diameter ranging from 0.01 to 5μ.

4. The composition of claim 2 wherein said vesicles have an average diameter ranging from 0.05 to 0.35μ.

5. The composition of claim 1 wherein said ionic amphiphilic lipid is a natural or synthetic phospholipid.

6. The composition of claim 1 wherein said ionic amphiphilic lipid is an amphoteric compound containing two lipophilic chains or a combination of two long-chain organic ions of opposite signs.

7. The composition of claim 1 wherein said ionic amphiphilic lipid is an anionic compound.

8. The composition of claim 7 wherein said ionic amphiphilic lipid is a compound having the formula $$R_1\text{—CHOH—CH—COA}$$
$$|$$
$$R_2\text{—CONH}$$

wherein
$R_1$ represents a $C_7$–$C_{21}$ alkyl or alkenyl radical,
$R_2$ represents a $C_7$–$C_{31}$ saturated or unsaturated hydrocarbon radical,
COA represents a member selected from the group consisting of
(i) COOM wherein M represents H, Na, K, $NH_4$ or a substituted ammonium ion derived from an amine,
(ii)

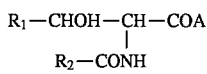

wherein B is a radical derived from a mono- or polyhydroxylated primary or secondary amine and $R_3$ represents hydrogen, methyl, ethyl or hydroxyethyl,
(iii)

wherein Q represents an aminoalkyl or ammonioalkyl radical and $R_3$ has the meaning given above, and
(iv) COOZ, wherein Z is the residue of a $C_3$–$C_7$ polyol.

9. The composition of claim 1 wherein said ionic amphiphilic lipid constituting said hydrated lipidic lamellar phase is present in combination with at least one stabilizer selected from the group consisting of a sterol, a monosodium salt of an acyl glutamate wherein the acyl moiety has 14–22 carbon atoms, a disodium salt of an acyl glutamate wherein the acyl moiety has 14–22 carbon atoms, a phosphoric ester of a $C_{12}$–$C_{16}$ fatty alcohol and oxyethylenated phytosterol.

10. The composition of claim 1 wherein said ionic amphiphilic lipid constituting said hydrated lipidic lamellar phase is present in combination with
(i) at least one anionic stabilizer present in an amount not exceeding 12 percent by weight based on the total weight of said ionic amphiphilic lipid, or
(ii) at least one sterol present in an amount not exceeding 100 percent by weight based on the total weight of said ionic amphiphilic lipid, or
both (i) and (ii).

11. The composition of claim 1 wherein said hydrated lipidic lamellar phase contains water in the presence or absence of a cosmetically or pharmaceutically active agent.

12. The composition of claim 11 wherein said active agent is selected from the group consisting of a hair loss-preventing agent, a hair growth stimulating agent, a retinoid, an anti-inflammatory agent, an antifungal agent, an anti-seborrheic agent and a sunscreen agent.

13. The composition of claim 1 wherein said cationic surface active agent present in said continuous aqueous phase is selected from the group consisting of
(a) a tetraalkylammonium halide,
(b) a stearamidopropyldimethyl (myristylacetate) ammonium chloride having the formula:

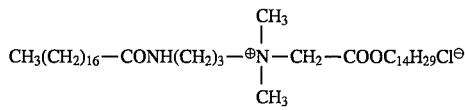

(c) a quaternary ammonium salt having the formula:

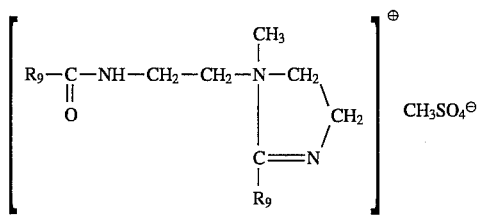

wherein
$R_9$ represents a mixture of (i) $C_{13}$–$C_{21}$ alkenyl radicals or (ii) of $C_{13}$–$C_{21}$ alkyl radicals, or both (i) and (ii), derived from tallow fatty acids.

14. The composition of claim 1 wherein said quaternized protein is selected from the group consisting of (a) an animal protein hydrolysate carrying, on the polypeptide chain, a quaternary ammonium group containing at least one $C_1$–$C_{18}$ alkyl radical, (b) an animal protein hydrolysate carrying a trimethylbenzylammonium group, (c) a collagen hydrolysate carrying a trimethylammonium group, (d) a collagen hydrolysate carrying a trimethylammonium group and a trimethylstearylammonium group and (e) a quaternized protein resulting from the condensation of cocamidopropyldimethylamine onto a hydrolyzed animal protein.

15. The composition of claim 1 which contains both at least one cationic surface active agent and at least one quaternized protein.

16. The composition of claim 15 which contains behenyltrimethylammonium chloride and an animal protein hydrolysate carrying, on the polypeptide chain, a quaternary ammonium group containing at least one $C_1$–$C_{18}$ alkyl chain, said polypeptide chain having an average molecular weight of approximately 12,000.

17. The composition of claim 1 wherein said continuous aqueous phase contains at least one additive selected from the group consisting of a preserving agent, a stabilizer, a colorant, a humectant, a softener, a perfume and a thickener.

18. The composition of claim 1 wherein said cationic surface active agent is present in an amount ranging from 0.05 to 10 percent by weight based on the total weight of said composition.

19. The composition of claim 1 wherein said cationic surface active agent is present in an amount ranging from 0.1 to 6 percent by weight based on the total weight of said composition.

20. The composition of claim 1 wherein said quaternized protein is present in an amount ranging from 0.05 to 3 percent by weight based on the total weight of said composition.

21. The composition of claim 1 wherein said quaternized protein is present in an amount ranging from 0.05 to 0.5 percent by weight based on the total weight of said composition.

22. The composition of claim 1 wherein said ionic amphiphilic lipid constituting said lamellar phase is present in an amount ranging from 0.1 to 20 percent by weight based on the total weight of said composition.

23. The composition of claim 1 wherein said ionic amphiphilic lipid constituting said lamellar phase is present in an amount ranging from 1 to 10 percent by weight based on the total weight of said composition.

24. The composition of claim 1 wherein said ionic amphiphilic lipid constituting said lamellar phase is present in an amount ranging from 3 to 10 percent by weight based on the total weight of said composition.

25. A process for treating the hair and scalp of a person so as to enable the hair to be untangled and styled without being softened or made heavy or greasy and to impart a hydrating action on the scalp, said process comprising topically applying to the hair and scalp 20 to 40 grams of the cosmetic composition of claim 1, permitting said composition to remain in contact with said hair and scalp for a period of time ranging from 1 to 15 minutes and then rinsing said hair and scalp with water.

26. A process for treating the hair and scalp of a person so as to enable the hair to be untangled and styled without being softened or made heavy or greasy and to impart a hydrating action on the scalp, said process comprising topically applying to the hair and scalp 5 to 10 grams of the cosmetic composition of claim 1.

* * * * *